(12) United States Patent
Kurosawa et al.

(10) Patent No.: US 6,867,424 B2
(45) Date of Patent: Mar. 15, 2005

(54) WAFER DEFECT INSPECTION MACHINE HAVING A DUAL ILLUMINATION SYSTEM

(75) Inventors: Toshirou Kurosawa, Hachioji (JP); Yuzo Katsuki, Hachioji (JP); Jun Takebayashi, Hachioji (JP)

(73) Assignee: Tokyo Seimitsu Co., Ltd., Tokyo (JP)

( * ) Notice: Subject to any disclaimer, the term of this patent is extended or adjusted under 35 U.S.C. 154(b) by 291 days.

(21) Appl. No.: 10/295,621

(22) Filed: Nov. 15, 2002

(65) Prior Publication Data

US 2003/0094586 A1 May 22, 2003

(30) Foreign Application Priority Data

Nov. 16, 2001 (JP) ........................................ 2001-351965

(51) Int. Cl.⁷ ............................................. G01N 21/86
(52) U.S. Cl. ..................... 250/559.4; 250/216
(58) Field of Search .................. 250/559.4, 559.45, 250/559.44, 216; 356/237.1, 237.4, 237.5, 239.3

(56) References Cited

U.S. PATENT DOCUMENTS 4,881,802 A * 11/1989 Stankewitz ................ 359/387
5,058,982 A 10/1991 Katzir

* cited by examiner

Primary Examiner—Que T. Le
(74) Attorney, Agent, or Firm—Christie, Parker and Hale, LLP

(57) ABSTRACT

A low-cost defect inspection machine for semiconductor wafers that can detect various defects has been disclosed and comprises an optical system that projects a pattern image, an image sensor and a processing circuit that processes the image signal and detects defect portions, wherein the optical system comprises an objective lens, a bright field illumination system that has a semi-transparent mirror and irradiates a specimen through the objective lens with the illumination light reflected by the semi-transparent mirror in the range that includes the optical axis of the objective lens, and a dark field illumination system that has a reflecting mirror provided in the portion except for the projection path of the objective lens and irradiates a specimen through the objective lens with the illumination light reflected by the reflecting mirror.

5 Claims, 4 Drawing Sheets

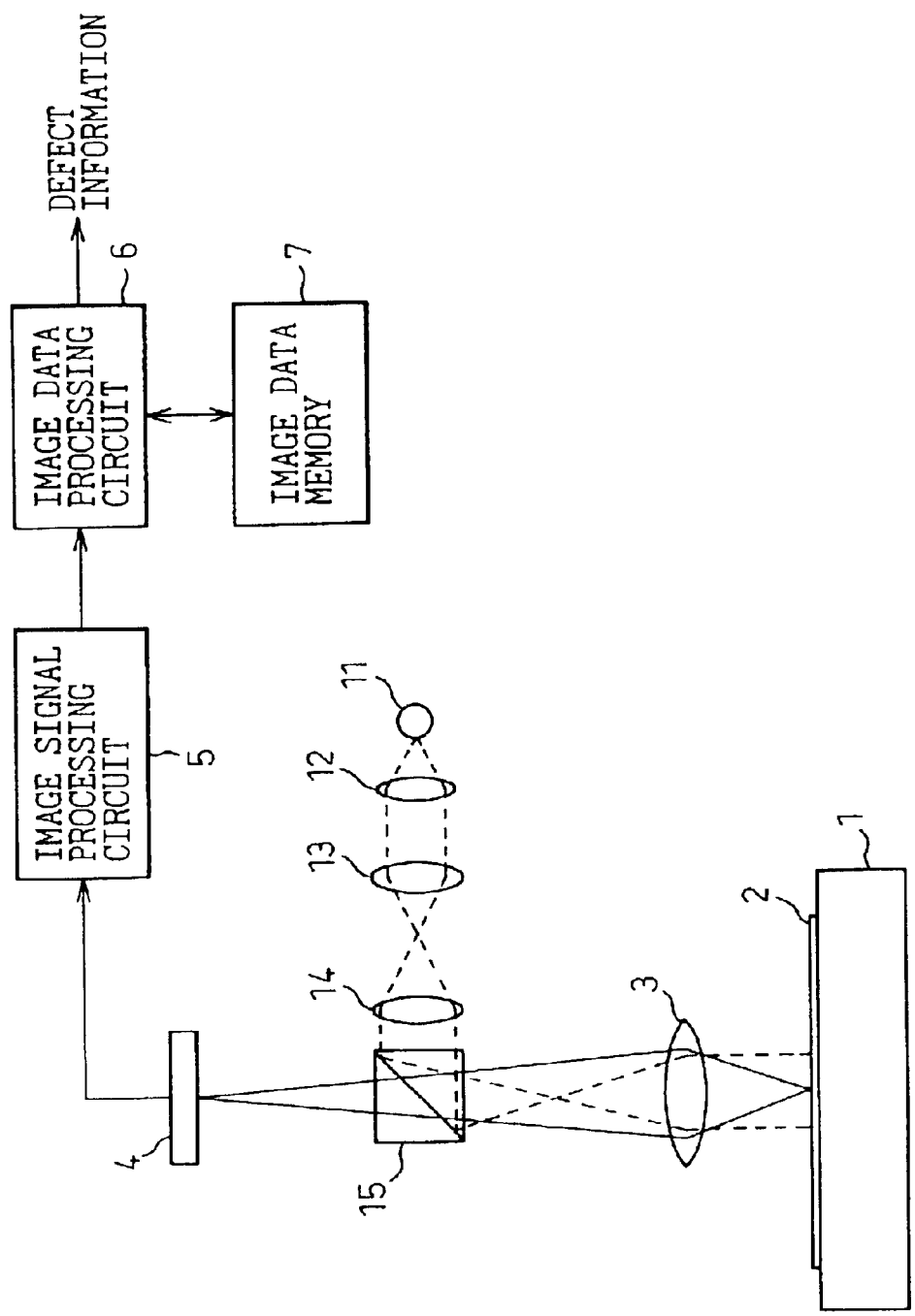

WAFER DEFECT INSPECTION MACHINE HAVING A DUAL ILLUMINATION SYSTEM

CROSS-REFERENCE TO RELATED APPLICATION

This application claims priority of Japanese Patent Application No. 2001-351965, filed Nov. 16, 2001.

BACKGROUND OF THE INVENTION

The present invention relates to a wafer defect inspection machine that captures an image of a pattern formed on a wafer and detects a defective portion by processing image signals. More particularly, the present invention relates to a structure of an illumination optical system.

Fixed patterns are formed repeatedly on semiconductor wafers, photomasks for semiconductor memories, liquid crystal display panels etc. In this case, optical images of these patterns are captured and defects of the patterns are detected by comparing neighboring patterns. If the result shows no difference between two patterns, it is judged that there is no defect in the two patterns, and if it shows a difference, it is judges that a defect exists in one pattern. As such a machine is generally called a wafer defect inspection machine, the term is also used here. Moreover, an example of a wafer defect inspection machine, for semiconductor wafers, that inspects for defects of patterns formed on a semiconductor wafer is described below. The present invention, however, is not limited to this but is applicable to a defect inspection machine for photomasks for semiconductor memories, for liquid crystal display panels etc.

FIG. 1 is a diagram that shows the rough structure of a defect inspection machine for semiconductor wafers. As shown in FIG. 1, the defect inspection machine for semiconductor wafers comprises a stage 1 that holds a semiconductor wafer 2, an objective lens 3 that projects the optical image of the surface of the semiconductor wafer 2, an image sensor 4 that converts the projected optical image of the surface of the semiconductor wafer 2 into electric image signals, an image signal processing circuit 5 that processes and converts the analog image signals output from the image sensor 4 into multi-valued digital image data, an image data processing circuit 6 that detects defects by processing the digital image data and comparing the same portion of patterns and an image data memory 7 that stores image data for data processing. The illumination optical system that illuminates the surface of the semiconductor wafer 2 comprises a light source 11, illumination lenses 12, 13 and 14, and a semi-transparent mirror (a beam splitter) 15 provided in the projection light path of the objective lens 3.

The illumination optical system in the defect inspection machine for semiconductor wafers is described below. In the defect inspection machine for semiconductor wafers, an illumination optical system of a metallographical microscope is used. As an illumination optical system of a metallographical microscope, a bright field illumination system as shown in FIG. 2A and a dark field illumination system as shown in FIG. 2B are known. In the bright field illumination system, the illumination light from a light source 21 is guided through a lens 22, an aperture stop 23, a lens 24, a field stop 25 and a lens 26, reflected toward the objective lens 3 by a semi-transparent mirror 27 provided in the projection path, and is directed to illuminate the surface of a specimen (wafer; through the objective lens 3. The lens 22 projects the image of the light source 22 on the position of the aperture stop 23 and the lenses 25 and 26 project the image on the position denoted by reference number 28. This position is the focal point of the objective lens 3 and uniform illumination without any unevenness in light quantity can be projected onto the surface of the wafer 2. Such illumination is called Koehler illumination. In the bright field illumination system, the surface of the wafer 2 is illuminated in the direction of the optical axis of the objective lens and the image of the regularly reflected light is captured.

In the dark field illumination system, on the other hand, the illumination light from a light source 31 is turned into an annular light flux by blocking its central portion and is further formed into an almost parallel light flux by the objective lens 3. This annular parallel light flux is directed into a perforated mirror 33 and formed into a light flux parallel to the optical axis of the objective lens 3. The perforated mirror 33 is an annular (more exactly, elliptic annular) reflecting mirror that allows light near the optical axis of the objective lens 3 to pass but reflects light of the peripheral portion. The annular illumination light reflected by the perforated mirror 33 enters a ring-shaped condenser lens 34 and illuminates the portion near the optical axis of the objective lens 3 of the wafer 2. In the dark field illumination system, an image of extremely high contrast can be obtained, but there is a problem that the image is not so bright because the illumination light regularly reflected by the surface of the wafer 2 cannot be captured.

There are metallographical microscopes equipped with both the bright field illumination system as shown in FIG. 2A and the dark field illumination system as shown in FIG. 2B. The bright portion and the dark portion, however, are opposite in the bright field illumination system and in the dark field illumination system and the images annihilate each other, therefore, one of the illumination systems is used according to the purpose. Devices such as a light source are, therefore, commonly used.

Moreover, there are dark field illumination systems in which the ring-shaped condenser lens, which is used in the dark field illumination system shown in FIG. 2B, is not used but means such as a reflecting mirror and optical fiber are used for illumination from the outside of the projection optical system of the objective lens, and such a dark field illumination system is used in a defect inspection machine for semiconductor wafers. It is, however, necessary to use an objective lens with a large NA (Numerical Aperture) in a defect inspection machine for semiconductor wafer because objects to be inspected have extremely fine patterns so, in the case of the illumination from the outside of the projection optical system, the incident angle of the illumination light becomes large. It is, therefore, impossible to illuminate the bottom part of the wafer pattern and a problem occurs that the defects in the pits of the patterns cannot be detected.

As described above, as the bright field illumination system and the dark field illumination system have both advantages and disadvantages, respectively, one of the illumination systems is used in a conventional defect inspection machine for semiconductor wafers according to the purpose of the inspection. Even if both the illumination systems are equipped, as described above, only one of them is used. U.S. Pat. No. 5,058,982 has disclosed a machine equipped with both the bright field illumination system and the dark field illumination system. FIG. 3 is a diagram that shows an example of the structure of the illumination optical system of the inspection machine disclosed in U.S. Pat. No. 5,058, 982. As shown in FIG. 3, in the dark field illumination system, the illumination light from a fiber light source 41 is reflected by a cylindrical mirror 43, the illumination light from a fiber light source 42 is reflected by a cylindrical mirror 44, and the specimen 2 is illuminated obliquely. In the bright field illumination system, on the other hand, the illumination light from the fiber light source 42 is converged by a lens 46, reflected by a beam splitter 47, and is directed to illuminate the specimen 2 vertically. The surface image of the illuminated specimen 2 is projected by the objective lens 3. The simultaneous use, however, of both the illumination optical systems has not been stated in U.S. Pat. No. 5,058,982.

In the case of this inspection machine, as the bright field illumination system and the dark field illumination system are arranged between the objective lens 3 and the specimen 2, an objective lens of a large NA cannot be used and the projection magnification cannot be made large and, therefore, a problem occurs that this machine is not proper when inspecting defects in semiconductor wafer patterns.

As described above, a typical conventional defect inspection machine has a structure in which a dark field illumination system is provided outside the projection optical system, therefore, a problem occurs that it is not suitable as a defect inspection machine for semiconductor wafer that inspects fine patterns. This leads to a suggestion that the bright field illumination system shown in FIG. 2A and the dark field illumination system shown in FIG. 2B are provided in a defect inspection machine for semiconductor wafer. There occurs, however, a problem that the cost is increased if two illumination systems are provided and there is another problem particularly in the dark field illumination system that the cost is further increased because it is necessary to provide a ring-shaped condenser lens in addition to an objective lens.

SUMMARY OF THE INVENTION

The objective of the present invention is to realize a defect inspection machine for semiconductor wafers that can detect various defects at a low cost.

In order to realize the above-mentioned objective, a wafer is irradiated with illumination light in the dark field illumination system through an objective lens in the defect inspection machine for semiconductor wafers of the present invention.

In other words, the defect inspection machine for semiconductor wafer of the present invention comprises: an optical system that projects an image of pattern formed on a wafer; an image sensor that converts the projected image into an image signal; and a processing device that detects defective parts by processing the image signal, wherein the optical system comprises: an objective lens; a bright field illumination system that has a semi-transparent mirror provided in the projection path of the objective lens and irradiates a specimen through the objective lens with the illumination light reflected by the semi-transparent mirror in the range that includes the optical axis of the objective lens; and a dark field illumination system that has a reflecting mirror provided in the portion except for the projection path of the objective lens and irradiates a specimen through the objective lens with the illumination light reflected by the reflecting mirror in the range except for the periphery of the optical axis of the objective lens.

In the defect inspection machine for semiconductor wafers of the present invention, the illumination light in the dark field illumination system is directed to irradiate a wafer through the objective lens, therefore, it is not necessary to provide a ring-shaped condenser lens, and the cost can be reduced accordingly. Moreover, irradiation is carried out through the objective lens and the incident angle of the illumination light in the dark field illumination system can be made even less compared to the case in which a ring-shaped condenser lens is used.

It is desirable that an illumination switching mechanism is provided for selecting to use either one or both of the bright field illumination system and the dark field illumination system. It is also desirable that the bright field illumination system and the dark field illumination system comprise a light quantity adjusting mechanism that adjusts the intensity of illumination light, respectively, and that the quantity of the bright field illumination light and that of the dark field illumination light can be adjusted independently. The light quantity adjusting mechanism can be realized by preparing ND filters of different concentrations so that the ND filters to be arranged in the illumination light path can be switched or by providing a variable aperture. The illumination light quantity can be also adjusted independently by providing a mechanism in which the bright field illumination system and the dark field illumination system comprise separate light sources, respectively, and the light emission quantity of each light source is adjusted independently by changing the voltage (current) to be applied to each light source.

As described above, the bright portion and the dark portion of an image are opposite in the bright field illumination system and in the dark field illumination system, and both are not used at the same time because each image annihilates each other. The present applicants, however, have discovered that the features of the patterns observed in the bright field illumination system and in the dark field illumination system, respectively, can be detected at the same time by adjusting each light quantity properly even if both the bright field illumination system and the dark field illumination system are used at the same time. Some patterns, however, cannot be detected when both the bright field illumination system and the dark field illumination system are used at the same time, therefore, it is important to adjust each illumination light quantity adequately by using the above-mentioned light quantity adjusting mechanism. If the pattern features observed respectively in the bright field illumination system and the dark field illumination system can be detected at the same time, the inspection time can be reduced accordingly.

BRIEF DESCRIPTION OF THE DRAWINGS

The features and advantages of the invention will be more clearly understood from the following description taken in conjunction with the accompanying drawings in which:

FIG. 1 is a diagram that shows the basic structure of a conventional defect inspection machine for semiconductor wafer.

DESCRIPTION OF THE PREFERRED EMBODIMENTS

Figure 4:
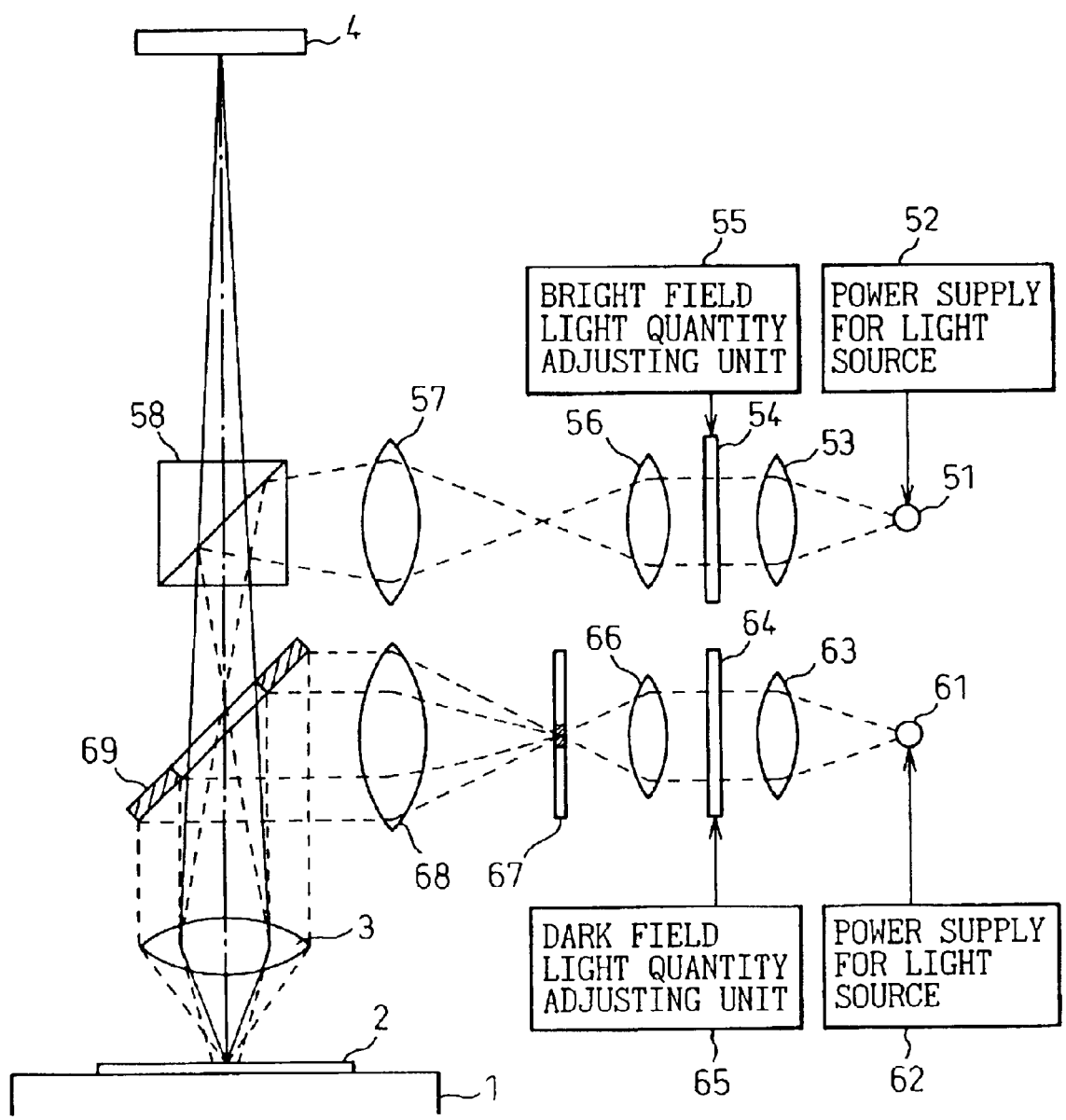
FIG. 4 is a diagram that shows the structure of the optical system of the defect inspection machine for semiconductor wafer in the embodiments of the present invention.

FIG. 4 is a diagram that shows the optical system of the defect inspection machine for semiconductor wafers in the embodiments of the present invention. Other parts shown in FIG. 1 are omitted here.

Figure 2A:
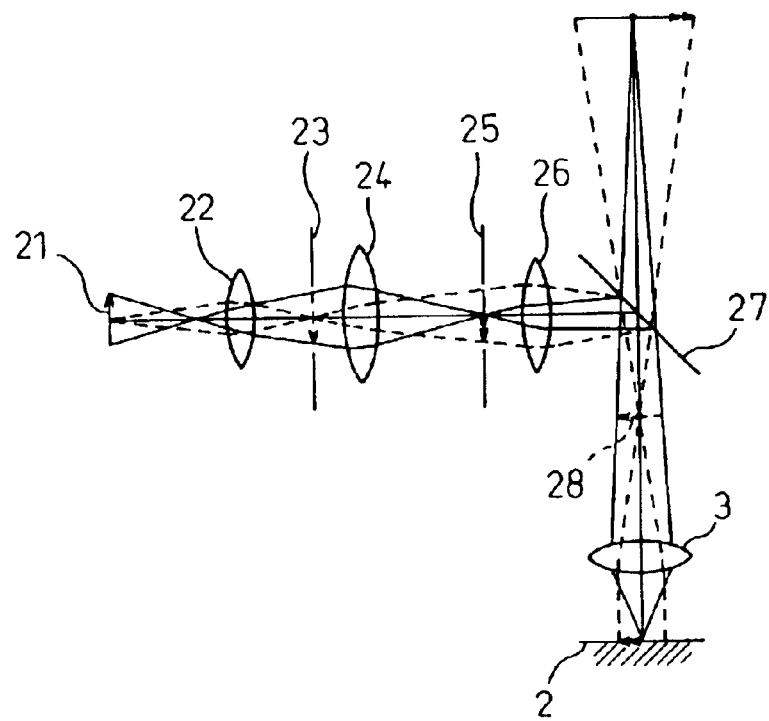
FIG. 2A is a diagram that illustrates the bright field illumination system of a metallographical microscope.
Figure 2B:
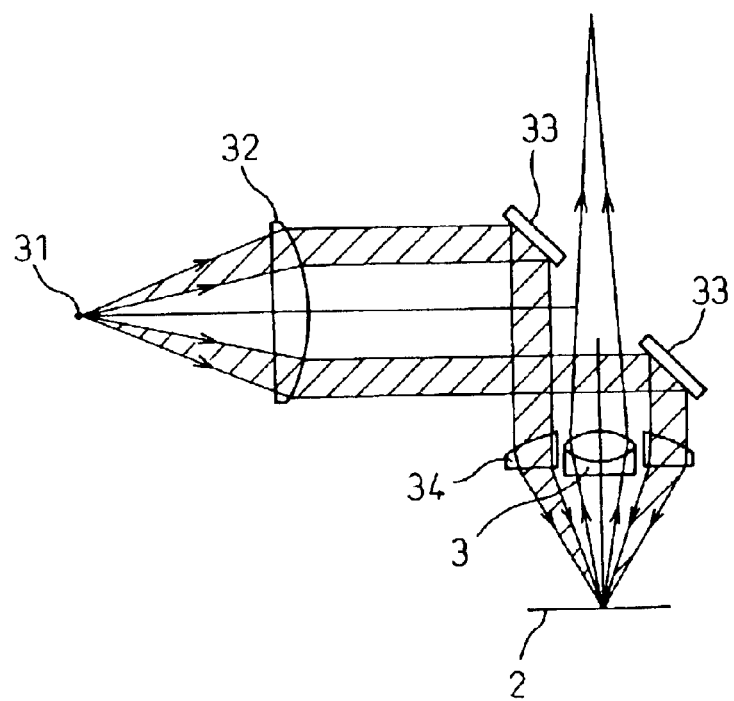
FIG. 2B is a diagram that illustrates the dark field illumination system of a metallographical microscope.
Figure 3:
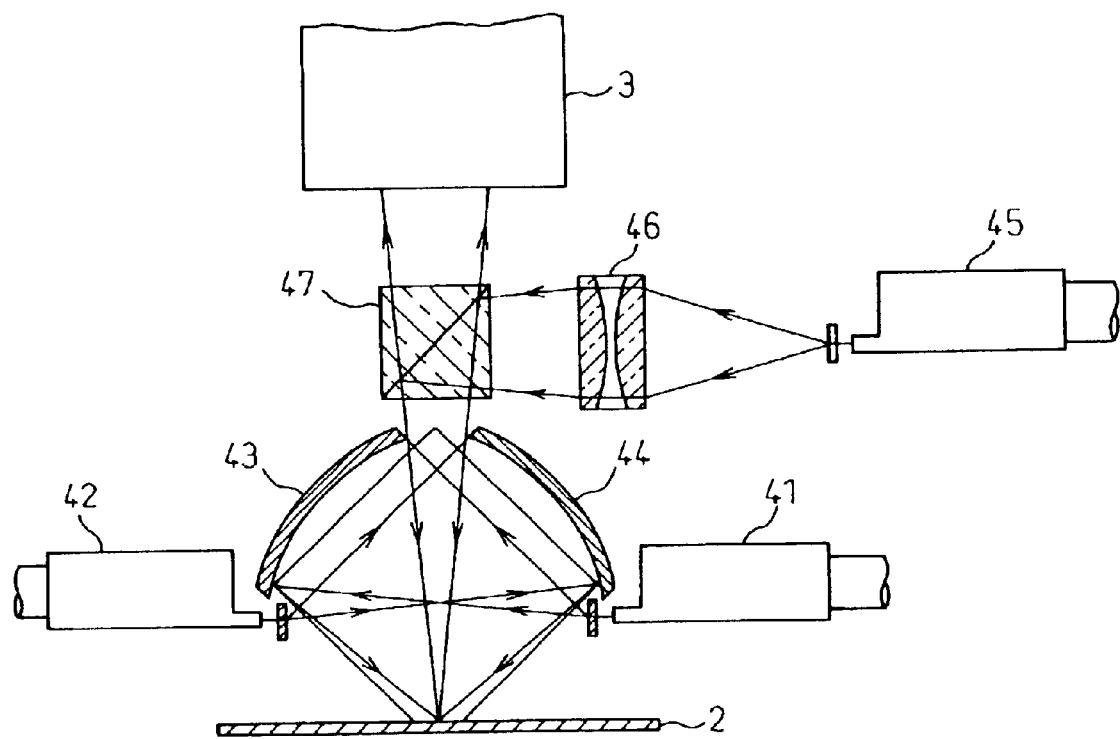
FIG. 3 is a diagram that shows the illumination system of a conventional defect inspection machine for semiconductor wafer that has both the bright field illumination system and the dark field illumination system.

As shown in FIG. 4, the defect inspection machine for semiconductor wafers in the present embodiment comprises the stage 1 that holds the semiconductor wafer 2, the objective lens 3 that projects the optical image of the surface of the semiconductor wafer 2, the image sensor 4 that converts the projected optical image of the surface of the semiconductor wafer 2 into electric image signals, a bright field illumination system and a dark field illumination system. The bright field illumination system comprises a light source 51, a power supply for light source 52, an illumination lens 53, a light quantity adjusting filter 54, a bright field light quantity adjusting unit 55, illumination lenses 56 and 57 and a semi-transparent mirror (a beam splitter) 58. Although apertures can be provided as in FIG. 2A, they are omitted here. The dark field illumination system comprises a light source 61, a power supply for light source 62, an illumination lens 63, a light quantity adjusting filter 64, a dark field light quantity adjusting unit 65, an illumination lens 66, a dark field illumination filter 67, an illumination lens 67 and a perforated mirror 69. The illumination paths in the bright field illumination system and the dark field illumination system are basically the same as the conventional ones shown in FIG. 2A and FIG. 2B, but it is important, and should be emphasized, that the light sources are provided separately and the light quantity adjusting filters 54 and 64 are provided.

The bright field light quantity adjusting unit 55 and the dark field light quantity adjusting unit 65 are provided with plural ND filters of different concentrations that correspond to the light quantity adjusting filers 54 and 64 on, for example, the rotating disc, and they are designed so that they can change the ND filters to be arranged on the light path to change the illumination light quantity by changing the rotation position. Moreover, the disc has a light-shielding plate instead of the ND filter, and the illumination light can be shielded and the illumination system can be brought into an inactivated state by arranging the disc in the light path so that the light-shielding plate cuts off the illumination light. In this way, it is possible to select use of one or both of the illumination systems.

The power for the light sources 51 and 61 is supplied from the power supply for light sources 52 and 62, respectively, and it is designed so that the light quantity can be changed by altering the voltage or current to be supplied. Moreover, if the supply of the power to the light source is terminated, it does not emit light, therefore, the illumination system can be brought into an inactivated state.

When it is selected to use one of or both the bright field illumination system and the dark field illumination system according to the type of a semiconductor wafer to be inspected, and if one of them is used, the light quantity adjusting mechanism needs to be adjusted to achieve an optimum state of illumination, and if both are used, both the light quantity adjusting mechanisms need to be adjusted at the same time to achieve an optimum state of illumination.

According to the present invention, as described above, a defect inspection machine for semiconductor wafer that can detect various defects can be realized at a low cost and particularly the pattern features observed in the bright field illumination system and the dark field illumination system can be detected in a brief inspection time.

We claim:

1. A wafer defect inspection machine comprising: an optical system to project a pattern image formed on a wafer; an image sensor to convert the projected image into an image signal; and a processing device to detect defect portions by processing the image signal, wherein the optical system comprises: an objective lens; a bright field illumination system, having a semi-transparent mirror provided in the projection path of the objective lens and irradiating said wafer through the objective lens with the illumination reflected by the semi-transparent mirror in the range that includes the optical axis of the objective lens; and a dark field illumination system, having a reflecting mirror provided in the portion except for the projection path of the objective lens and irradiating said wafer through the objective lens with the illumination light reflected by the reflecting mirror in the range except for the periphery of the optical axis of the objective lens.

2. A wafer defect inspection machine, as set forth in claim 1, wherein an illumination switching mechanism for selecting to use either one or both of the bright field illumination system and the dark field illumination system is provided.

3. A wafer defect inspection machine, as set forth in claim 1, wherein the bright field illumination system and the dark field illumination system comprise each a light quantity adjusting mechanism to adjust the intensity of illumination light and the quantity of the bright field illumination light and that of the dark field illumination light can be adjusted independently.

4. A wafer defect inspection machine, as set forth in claim 1, wherein the bright field illumination system and the dark field illumination system comprise each a light source.

5. A wafer defect inspection machine, as set forth in claim 4, wherein the bright field illumination system and the dark field illumination system each comprise a mechanism to adjust the light emission quantity of each light source independently.

* * * * *